United States Patent [19]

Truckai

[11] Patent Number: 5,176,660
[45] Date of Patent: Jan. 5, 1993

[54] CATHETER HAVING REINFORCING STRANDS

[75] Inventor: Csaba Truckai, Miami, Fla.

[73] Assignee: Cordis Corporation, Miami Lakes, Fla.

[21] Appl. No.: 666,601

[22] Filed: Mar. 8, 1991

Related U.S. Application Data

[62] Division of Ser. No. 424,927, Oct. 23, 1989, Pat. No. 5,019,057.

[51] Int. Cl.⁵ ............................................. A61M 25/00
[52] U.S. Cl. .................................. 604/282; 138/123; 138/129; 138/133
[58] Field of Search ................. 604/95, 264, 280, 282; 128/658; 138/123-125, 127, 129-133; 87/1, 6, 8

[56] References Cited

U.S. PATENT DOCUMENTS

| | | | |
|---|---|---|---|
| 2,268,321 | 12/1941 | Flynn | 604/282 |
| 3,007,497 | 11/1961 | Shobert | 138/125 |
| 3,022,802 | 2/1962 | Lewis | 138/125 |
| 3,416,531 | 12/1968 | Edwards | |
| 3,485,234 | 12/1969 | Stevens | |
| 3,498,286 | 3/1970 | Polanyi et al. | 604/282 |
| 3,585,707 | 6/1971 | Stevens | |
| 3,739,770 | 6/1973 | Mori | 138/130 |
| 3,924,632 | 12/1975 | Cook | 604/282 |
| 4,176,662 | 12/1979 | Frazer | 604/280 |
| 4,425,919 | 1/1984 | Alston, Jr. et al. | |
| 4,567,917 | 2/1986 | Millard | 138/127 |
| 4,690,175 | 9/1987 | Ouchi et al. | 604/282 |
| 4,705,511 | 11/1987 | Kocak | 604/282 |
| 4,817,613 | 4/1989 | Jaraczewski | 604/282 |
| 5,037,404 | 8/1991 | Gold et al. | |

Primary Examiner—John D. Yasko
Assistant Examiner—Anthony Gutowski
Attorney, Agent, or Firm—Gerstman & Ellis, Ltd.

[57] ABSTRACT

A flexible catheter comprises at least one resilient, tubular layer in telescoping relation with a tubular sheath made of helically disposed crossing strands. At least one of the strands has a width that substantially exceeds its height, preferably having a width that is 4 to 8 times greater than its height. Some of the strands are circular in cross-section. The Catheter also includes at least one permanently emplaced reinforcing filament carried generally parallel to the axis of the catheter, to increase the longitudinal stiffness of at least a portion of the catheter.

14 Claims, 1 Drawing Sheet

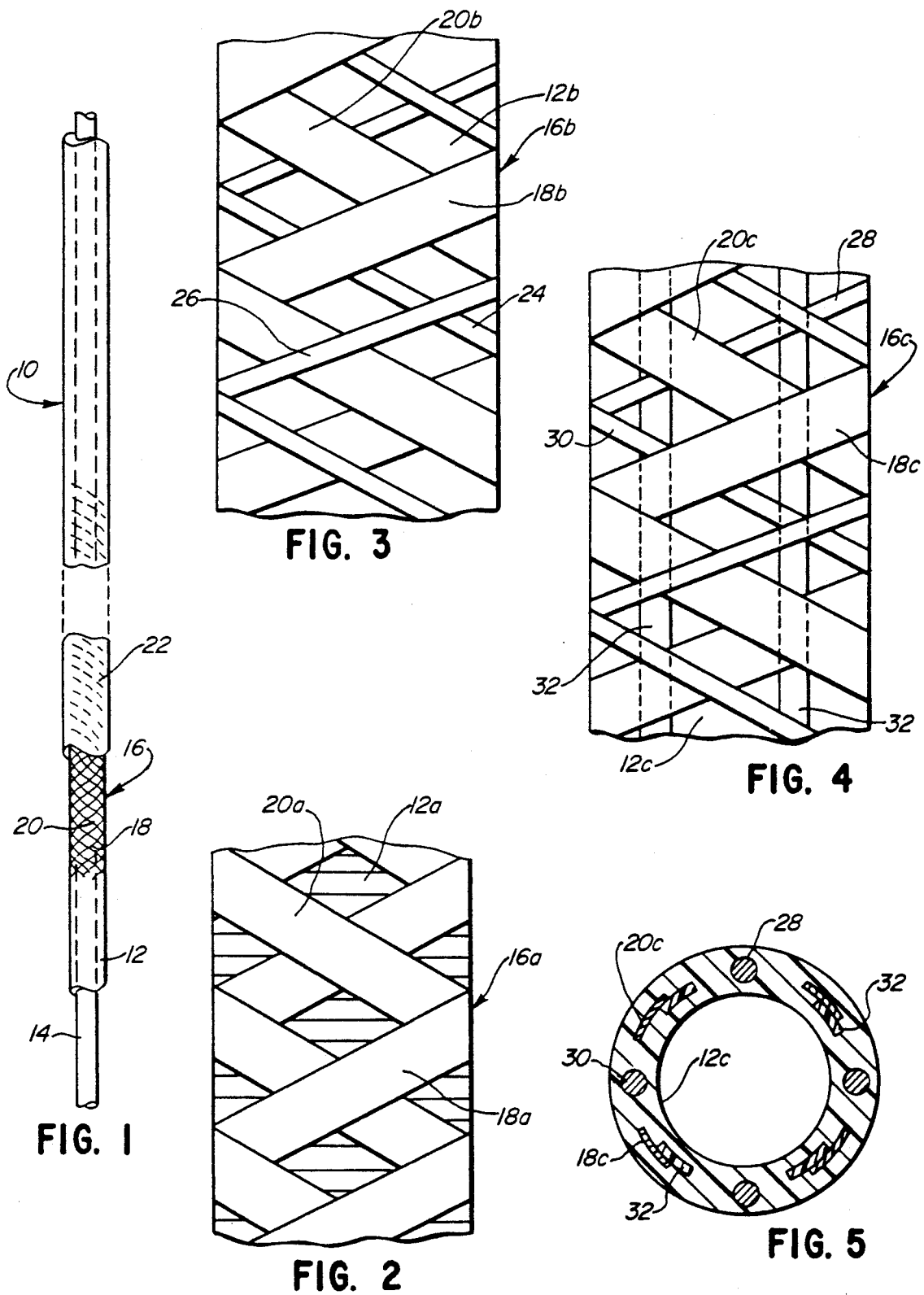

CATHETER HAVING REINFORCING STRANDS

This is a division of application Ser. No. 424,927, filed Oct. 23, 1989 (now U.S. Pat. No. 5,019,057).

BACKGROUND OF THE INVENTION

In Stevens U.S. Pat. Nos. 3,485,234 and 3,585,707, tubular products such as catheters are disclosed which comprise an extruded plastic coating having a tubular, braided wire sheath disposed tightly about a plastic coating in telescoping relation therewith. A second, extruded layer of plastic is then applied over the braided sheath.

Such a catheter, having a braided sheath, can increase both the longitudinal and the torsional stiffness of the catheter. Thus, at least a main portion of the catheter body may be longitudinally stiffened to facilitate the insertion of arteriovenous catheters, for example. An improved torsional stiffness permits torque to be better transmitted from the proximal end of the catheter to typically the distal tip. Such a characteristic is desirable to facilitate advancement of, for example, an intravascular catheter through a branching blood vessel system of a patient. As the catheter is advanced, the surgeon may rotate the proximal end, and, when a catheter has improved torsional stiffness, the distal end 20 more accurately follows the desired rotational movement imparted to the catheter by the surgeon.

The braided wire which is currently applied to catheters may increase or decrease both the longitudinal stiffness and the torsional stiffness in a manner which varies with the angle that the crossing strands exhibit to each other and to the axis of the catheter. However, the longitudinal stiffness increases when the strand angles to the catheter axis are reduced while the torsional stiffness increases with increasing angles of the strands to the catheter axis. Thus, one must sacrifice torsional stiffness in order to obtain good longitudinal stiffness while one must sacrifice longitudinal stiffness in order to get good torsional stiffness, depending upon the angles of the strands.

By this invention, an improved tubular sheath is provided to catheters, in which the sheath is made of helically disposed crossing strands in a manner analogous to the prior art, but with differences in the structure which permits increases in both the torsional and the longitudinal stiffness of the catheter in a desired but controllable manner. Thus, catheters of new and desired characteristics may be produced by this invention, which catheters were effectively unavailable in accordance with the techniques of the prior art.

DESCRIPTION OF THE INVENTION

In this invention a flexible catheter comprises at least one resilient, tubular layer in telescoping relation with a tubular sheath made of helically disposed crossing strands. Typically the strands are in braided relation in a manner analogous to the prior art. By this invention, at least one of the strands has a width that substantially exceeds its height, so that the strand is rather like tape or strapping rather than like wire of circular cross section. Thus, the strand described above defines a pair of opposed, major sides, one of the major sides facing the axis of the catheter along its entire length. This is to say that the wide, flat strands used in accordance with this invention are wound in helical manner about the catheter, preferably without twisting over, which would provide an undesirable twisted outward projection of the flat strands of this invention, adding to the width of the catheter and exhibiting other undesirable characteristics as well.

To prevent accidental twisting of the flat strands of this invention as they are wound about a resilient tubular catheter layer, the flat strands of this invention desirably have a width that is at least four times greater than their height. This tends to eliminate accidental twisting over of the strands as they are being helically wound into the catheter. It is also generally desirable for the width of the strands to be no more than eight times greater than their height, so that the flat strands do not substantially crimp and wrinkle as they are helically wound about the catheter.

Preferably, the tubular sheath is made of at least some metal strands, preferably spring steel, and most preferably all of the flat strands used herein ar made of spring steel. However, if desired, biaxially oriented plastic may be used as a strand material, or other appropriate structural materials known to the art.

Preferably, the tubular sheath of helical strands is sealed between inner and outer resilient, tubular layers. The respective layers may be bonded to each other between the interstices of the helical, crossing strands, so that there is no necessity to provide direct adhesion between the strands and one or both of the resilient, tubular layers. Typically, the tubular sheath is mechanically retained between the resilient tubular layers, although, if desired, an appropriate primer may be applied to the strands to improve their adhesion to the respective tubular layers.

In one embodiment, all of the crossing strands present in the tubular sheath may be of the wide, flat type which have widths that substantially exceed their heights. However, in a second embodiment, some of the strands present in the tubular sheath may be of substantially circular cross section.

In a third embodiment, the crossing strands of the tubular sheath may be associated with one or more reinforcing filaments Which are carried in the catheter generally parallel to the axis thereof. Such reinforcing filaments ca be used to increase the longitudinal stiffness in the catheter for even better "pushability", that is, the ability to insert the catheter by pushing it from its proximal end. Such reinforcing filaments may be made of a biaxially oriented thermoplastic material, and may be present on any portion of the catheter where the longitudinal stiffness is desired to be improved, or the whole catheter, if desired. Such materials may include biaxially oriented nylon, or polyester such as DuPont HYTREL.

As previously mentioned, the strands are preferably helically wound on a resilient tubular layer, preferably at a tension of at least 250,000 pounds per square inch (p.s.i.) of strand cross-sectional area, and typically no more than about 350,000 p.s.i., referring to the total tension imposed between the catheter and all strands being applied thereto.

Typically, the flat strands used in this invention have a width of 0.006 to 0.02 inch and a height 0.0015 to 0.004 inch, the width of such strands being typically at least 4 times greater than their height.

Accordingly, the various embodiments of the catheter of this invention may exhibit improved longitudinal and torsional stiffness, but in a manner which permits the selection of respective longitudinal and torsional stiffness in a manner which is relatively independent from each other. Accordingly, catheters having new physical characteristics may be provided for improved medical procedures.

The term "catheter", is intended to include all kinds of medical tubing, and including stents, which may also make use of the invention of this application and are intended to be covered herein.

If desired, the angles between the crossing strands of the tubular sheath of this invention may be varied at differing positions along a catheter made in accordance with the teachings herein, in a manner which is analogous to and more fully described by Gold et al. U.S. patent application Ser. No. 270,810, filed Nov. 14, 1988 and entitled CATHETER HAVING SECTIONS OF VARIABLE TORSION CHARACTERISTICS, now U.S. Pat. No. 5,037,404. By this expedient of varying of the respective strand angles, differing sections of the same catheter may exhibit differing physical characteristics.

DESCRIPTION OF THE DRAWINGS

Referring to the drawing, FIG. 1 is a fragmentary, plan view of the catheter in accordance with this invention, with portions broken away.

FIG. 2 is an enlarged, fragmentary, plan view of one embodiment of a catheter with its outer tubular removed, carrying a specific tubular sheath in accordance with this invention.

FIG. 3 is a fragmentary, plan view of another embodiment of catheter with its outer tubular layer removed, using another type of tubular sheath of this invention.

FIG. 4 is a fragmentary, plan view of yet another embodiment of catheter of this invention with its outer tubular layer removed.

FIG. 5 is a schematic sectional view.

DESCRIPTION OF SPECIFIC EMBODIMENTS

Referring to FIG. 1, a catheter 10 in accordance with this invention is shown. The specific catheter is made in accordance with the above-cited Stevens Patent, with an inner plastic extrusion 12, forming an inner, resilient tubular layer, being extruded on a mandrel 14 such as a silver wire. Inner plastic extrusion 12 may be made of any appropriate material which is desirably used for a catheter, such as polyethylene, nylon, PVC, polyurethane, or silicone rubber.

Either before or after curing inner extrusion 12 on mandrel 14, it may be placed into a conventional wire braiding machine to form a tubular braided wire sheath 16 about the outer surface of inner extrusion 12. The braided sheath 16 corresponds to the "tubular sheath" as described above. The braid may be laid down on inner extrusion 12 in the form of a set of counterrotating helical strands 18, 20, one of which set of strands rotates clockwise and the other counterclockwise. The braided strand arrangement may be conventional in configuration, except as otherwise taught herein.

Then an outer tubular layer 22 may be applied by extrusion over the braided tubular sheath 16, typically with some of the material of outer tubular layer 22 passing through the interstices of sheath 16 to enter into bonded relation with the material of inner tubular layer 12, to provide a strong, bonded catheter containing the desired sheath 16 of this invention.

FIG. 2 shows a short length of the catheter of FIG. 1 in a first embodiment, with outer tubular layer 22 removed. As shown, the tubular sheath 16a is made of helically disposed, crossing flat strands 18a, 20a, which are typically made of spring steel, being wound about an inner, resilient tubular layer 12a which may be made of polyurethane or the like. Strands 18a, 20a may be of dimension such as 0.002 by 0.008 inch or as another embodiment, 0.0025 by 0.013 inch. They may be wound about inner tubular layer 12a in a conventional braiding machine at a total tension of about 300,000 p.s.i. while inner tubular layer 12a is mounted on silver mandrel 14. Inner tubular layer 12a is of a typical outer diameter of about 0.068 in.. It should be noted that, generally, an increase in tension is required to effectively apply the flat braiding wire of this invention, when compared with conventional braiding operations, to assure proper laying down of the flat braiding wire without its twisting over onto its other side.

The catheter made in accordance with FIG. 2 exhibits excellent physical characteristics, including improved longitudinal and torsional stiffness. This stiffness can be adjusted to desired values by appropriate adjustment of the dimension of the flat strands used, and their strand angle to each other and the longitudinal axis of the catheter.

Referring to FIG. 3, the catheter of FIG. 1 is shown in a second embodiment, again with outer tubular layer 22 removed for clarity.

In this embodiment, tubular sheath 16b may comprise a mixture of helically disposed crossing flat, spring steel wires which cross each other in helically rotating and helically counterrotating relationships, specifically helically rotating flat wires 18b and helically counterrotating flat wires 20b. Also, there is added to tubular sheath 16 a plurality of helically rotating and counterrotating conventional wires of generally round cross section 24, 26, in braided helically wound relationship with the flat wires 18b, 20b. The flat wires may be of dimensions similar to the previous embodiment, while the round wires, made also of spring steel, may have an outer diameter of about 0.003 inch, for example. Additionally, the flat and round wires may be made of Nitnol band "Memory Wire", which wire can assume a predetermined shape upon heating to a certain temperature (or by electrical stimulation), so that the cool, straight catheter can be designed to form a desired curve after implantation as it is warmed by the body.

As a further advantage of this embodiment, the excellent torsional and longitudinal stiffness of the flat wire 18b, 20b is provided to the catheter, while the interstices between the wires to expose inner tubular layer 12b can be relatively enlarged by the presence of the mixed types of wire, for better bonding between inner layer 12b and outer layer 22. Round wires 24, 26 can lift the flat wires away from the surface of tubular layer 12b, to cause plastic material from outer layer 22 to find more surface contact with layer 12b.

This particular embodiment of wire sheath finds good utility for use as a stent, providing a smoother surface.

FIGS. 4 and 5 show another embodiment of the catheter of FIG. 1 in which inner, resilient, tubular layer 12c is surrounded by tubular sheath 16c which comprises a mixture of flat strands 18c, 20c and round strands 28, 30 in a manner similar to FIG. 3. Additionally, the catheter of FIG. 4 carries a plurality of four biaxially oriented plastic 15 reinforcing filaments 32 which may be made of nylon, for example, and which are positioned generally parallel to the axis of the catheter. Filaments 32 are seen to be retained against inner tubular layer 12c by the winding of strands 18c, 20c, 28, and 30, and serve to provide additional longitudinal stiffness to the catheter. If desired, the embodiment of FIG. 4 may utilize only flat, thin strands similar to strands 18c, 20c or only round strands similar to strands 28, 30 in the helically disposed tubular sheath 16.

Then, as before, outer layer 22 is applied, bonding to inner tubular layer 12c between the strand interstices to seal the various strands and filaments in place. Strands 18c, 20c may be of a type used in a previous embodiment.

Thus, high strength catheters of good rotational and longitudinal stiffness may be provided in accordance with this invention.

The above has been offered for illustrative purposes only, and is not intended to limit the scope of the invention of this application which is as defined in the claims below.

That which is claimed is:

1. A flexible catheter which comprises at least one resilient, tubular layer in telescoping relation with a tubular sheath made of helically disposed crossing strands, at least one of said strands having a width that substantially exceeds its height, and at least one strand defining a pair of opposed, major sides, one of said major sides facing along its entire length the axis of said catheter, said at least one strand being helically wound on said resilient tubular layer at a total tension of at least 250,000 p.s.i., said catheter also including at least one permanently emplaced reinforcing filament carried generally parallel to the axis of said catheter, to increase the longitudinal stiffness of at least a portion of the catheter, some of said strands present being of substantially circular cross-section.

2. The catheter of claim 1 in which said tubular sheath is made of at least some metal strands.

3. The catheter of claim 1 in which said tubular sheath is sealed between an inner and an outer of said resilient, tubular layers.

4. The catheter of claim 1 in which all of said crossing strands present have widths that substantially exceed their heights.

5. The catheter of claim 1 in which said at least one strand present is made of spring steel.

6. The catheter of claim 1 in which said at least one strand present has a width of 0.006 to 0.02 inch and a height of 0.0015 to 0.004 inch, the width of said one strand being at least 4 times greater the its height.

7. The catheter of claim 1 in which said reinforcing filament is made of a biaxially oriented thermoplastic.

8. The catheter of claim 1 in which said total tension is no more than about 350,000 p.s.i..

9. A flexible catheter which comprises at least one resilient, tubular layer in telescoping relation with a tubular sheath made of helically disposed crossing strands, at least one of said strands having a width that is 4 to 8 times greater than its height, said at least one strand defining a pair of opposed major sides, one of said major sides facing along its entire length the axis of said catheter, said at least one strand being helically wound on said resilient, tubular layer at a total tension of at least 250,000 p.s.i., said catheter also carrying at least one permanently emplaced reinforcing filament generally parallel to the axis of said catheter, to increase the longitudinal stiffness of at least a portion of the catheter, some of the strands present being of substantially circular cross-section.

10. The catheter of claim 9 in which said tubular sheets is sealed between an inner and an outer of said resilient, tubular layers.

11. The catheter of claim 10 in which all of said crossing strands present have width that substantially exceed their heights.

12. The catheter of claim 9 in which said reinforcing filament is made of a biaxially oriented thermoplastic.

13. The catheter of claim 10 in which said at least one strand is made of spring steel.

14. The catheter of claim 9 in which said total tension is no more than about 350,000 p.s.i..

* * * * *